United States Patent
Yoshioka et al.

(10) Patent No.: US 7,354,500 B2
(45) Date of Patent: Apr. 8, 2008

(54) MASK AND APPARATUS USING IT TO PREPARE SAMPLE BY ION MILLING

(75) Inventors: Tadanori Yoshioka, Tokyo (JP); Eiichi Watanabe, Tokyo (JP)

(73) Assignees: Jeol Ltd., Tokyo (JP); Jeol Engineering Co., Ltd., Tokyo (JP)

( * ) Notice: Subject to any disclaimer, the term of this patent is extended or adjusted under 35 U.S.C. 154(b) by 289 days.

(21) Appl. No.: 10/922,363

(22) Filed: Aug. 20, 2004

(65) Prior Publication Data

US 2005/0081997 A1  Apr. 21, 2005

(30) Foreign Application Priority Data

Aug. 20, 2003   (JP)   ............... 2003-296332

(51) Int. Cl.
  *C23F 1/00*    (2006.01)
  *H01J 37/08*   (2006.01)
  *C23C 16/00*   (2006.01)
  *C23C 16/04*   (2006.01)

(52) U.S. Cl. ............... 156/345.39; 156/345.3; 118/721; 118/505; 422/99; 250/492.21

(58) Field of Classification Search ............ 156/345.3, 156/345.39; 250/505.1, 492.21; 118/720, 118/721, 504, 505; 422/99
See application file for complete search history.

(56) References Cited

U.S. PATENT DOCUMENTS

| | | | | |
|---|---|---|---|---|
| 4,370,556 A | * | 1/1983 | Stengl et al. | 250/503.1 |
| 4,887,282 A | * | 12/1989 | Mueller | 378/34 |
| 4,891,547 A | * | 1/1990 | Stengl et al. | 313/407 |
| 5,831,272 A | * | 11/1998 | Utsumi | 250/492.2 |
| 5,876,880 A | * | 3/1999 | Vonach et al. | 430/5 |
| 5,907,157 A | | 5/1999 | Yoshioka et al. | |
| 7,158,701 B2 | * | 1/2007 | Dautartas | 385/37 |
| 2003/0087471 A1 | * | 5/2003 | Shtein et al. | 438/82 |
| 2005/0081997 A1 | * | 4/2005 | Yoshioka et al. | 156/345.3 |
| 2005/0118065 A1 | * | 6/2005 | Hasegawa et al. | 422/99 |
| 2006/0113496 A1 | * | 6/2006 | Yoshioka | 250/492.21 |
| 2006/0255295 A1 | * | 11/2006 | Yoshioka et al. | 250/492.21 |

FOREIGN PATENT DOCUMENTS

| | | | |
|---|---|---|---|
| JP | 62-31854 | * | 2/1987 |
| JP | 3263920 | | 8/1997 |
| JP | 2000-133857 | * | 5/2000 |

* cited by examiner

*Primary Examiner*—Jeffrie R Lund
(74) *Attorney, Agent, or Firm*—The Webb Law Firm

(57) ABSTRACT

A mask for use with a sample preparation apparatus that prepares an ion-milled sample adapted to be observed by an electron microscope is offered. It is possible to prepare the sample having a desired cross section by the use of the mask. The mask, which defines the boundary between irradiated and unirradiated regions on the sample surface, has an edge portion having an increased thickness compared with the other portions. When the edge portion of the mask is etched, the original shape is almost maintained. Thus, the side surface of the mask is kept on the center axis of the ion beam.

3 Claims, 4 Drawing Sheets

(DIAGRAM ILLUSTRATING ION PATH)

(PERSPECTIVE VIEW)

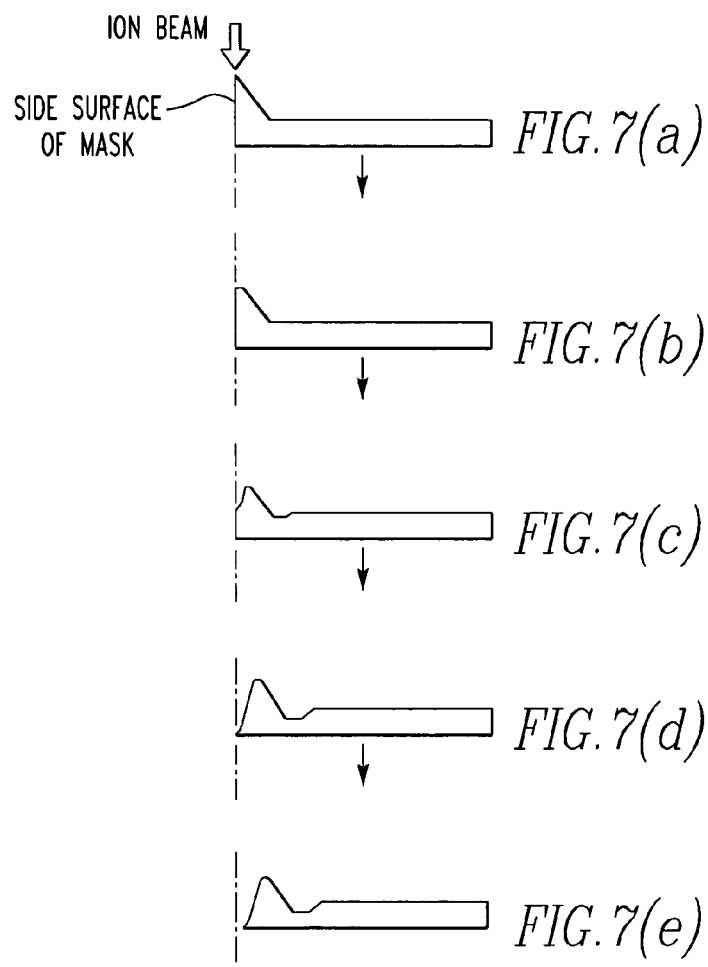
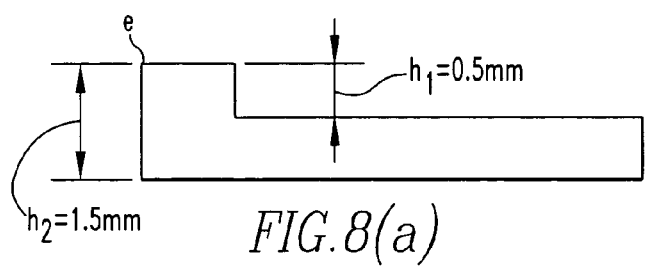
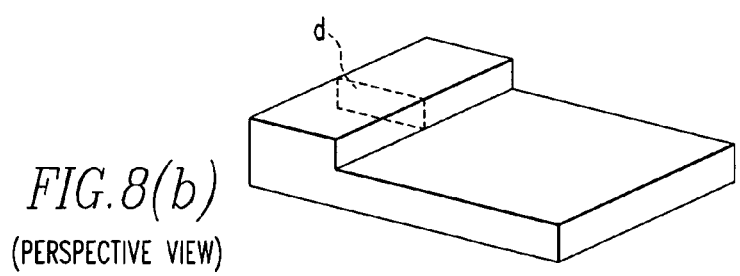

MASK AND APPARATUS USING IT TO PREPARE SAMPLE BY ION MILLING

BACKGROUND OF THE INVENTION

1. Field of the Invention

The present invention relates to a mask placed between a sample and the ion gun of a sample preparation apparatus utilizing ion milling. The invention also relates to this sample preparation apparatus having the mask.

2. Description of Related Art

One known apparatus for preparing ion-milled samples on a scanning electron microscope (SEM) or transmission electron microscope (TEM) is described, for example, in Japanese Patent No. 3263920. This known apparatus is now described by referring to FIG. 1. The apparatus uses a mask in the form of a flat plate. This mask is made of a shielding material, has a straight edge, and is placed over a sample. The sample is etched by an ion beam directed at it with the boundary defined by the edge of the mask. The hatched portion in the figure is a portion of the sample to be etched to obtain a sample cross section S.

FIGS. 2(a)-2(d) show the process in which the sample is etched by the apparatus shown in FIG. 1. In the initial phase of the etching, see FIG. 2(a), the sample is etched from its one corner. At the same time, the mask irradiated with the ion beam is etched from its one corner in the same way as the sample.

When the corner of the mask is etched and becomes rounded in this way, ions hitting the rounded portion slide down along the side surface of the mask, as illustrated in FIG. 2(d), the "diagram illustrating ion path". As a result, the ions travel longer distances (longer ion path lengths). Consequently, every ion etches the side surface of the mask over a longer distance. On the other hand, ions hitting the top surface of the mask are stopped there and thus the ion path length is quite small. As a result, the amount by which the rounded side surface of the mask is etched is considerably greater than the amount by which the top surface is etched.

Through the state shown in FIG. 2(b), the sample and mask are finally etched as shown in FIG. 2(c). Since the side surface of the mask has been etched considerably as shown in FIG. 2(c), the portions of the sample closer to the mask are overetched. That is, a portion of the sample including the desired cross section S is etched.

SUMMARY OF THE INVENTION

It is an object of the present invention to provide a mask and a sample preparation apparatus capable of preparing a sample having a desired cross section by the use of the mask and by ion milling.

This mask for the sample preparation apparatus that achieves the above-described object is placed on the sample surface irradiated with an ion beam and has an edge portion that defines the boundary between a region irradiated with ions and an unirradiated region on the surface of the sample. The edge portion is made thicker than the other portions.

Accordingly, the present invention provides the mask that is for use with the sample preparation apparatus and permits preparation of a sample having a desired cross section. The sample preparation apparatus is also offered.

Other objects and features of the invention will appear in the course of the description thereof, which follows.

BRIEF DESCRIPTION OF THE DRAWINGS

FIGS. 7(a)-7(e) illustrate a process in which etching is done using the mask shown in FIGS. 6(a) and 6(b); and FIGS. 8(a) and 8(b) illustrate another mask according to the present invention.

DESCRIPTION OF THE PREFERRED EMBODIMENTS

Embodiments of the present invention are hereinafter described with reference to the accompanying drawings.

Figure 1:
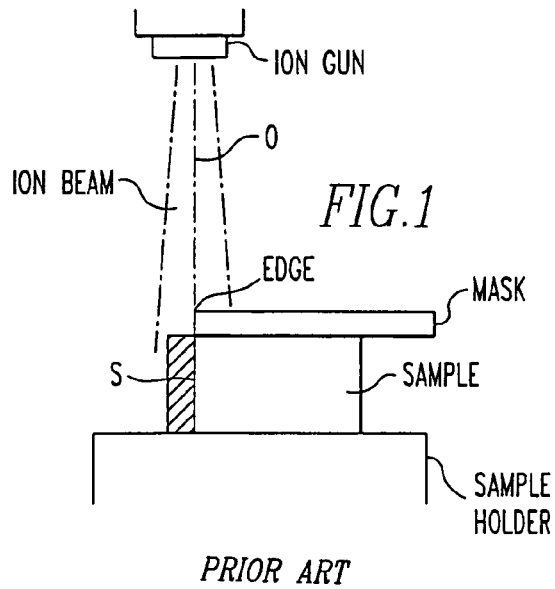
FIG. 1 is a diagram illustrating a conventional sample preparation apparatus utilizing ion milling.
Figure 2A:
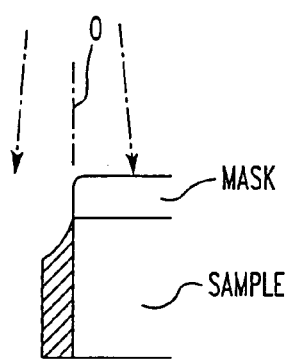
FIGS. 2(a)-2(d) illustrate a process in which a sample is etched by the apparatus shown in FIG. 1.
Figure 2B:
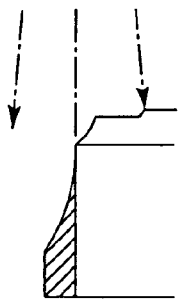
Figure 2D:
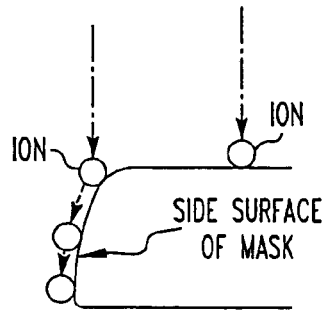
Figure 2C:
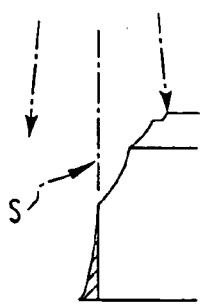
Figure 3:
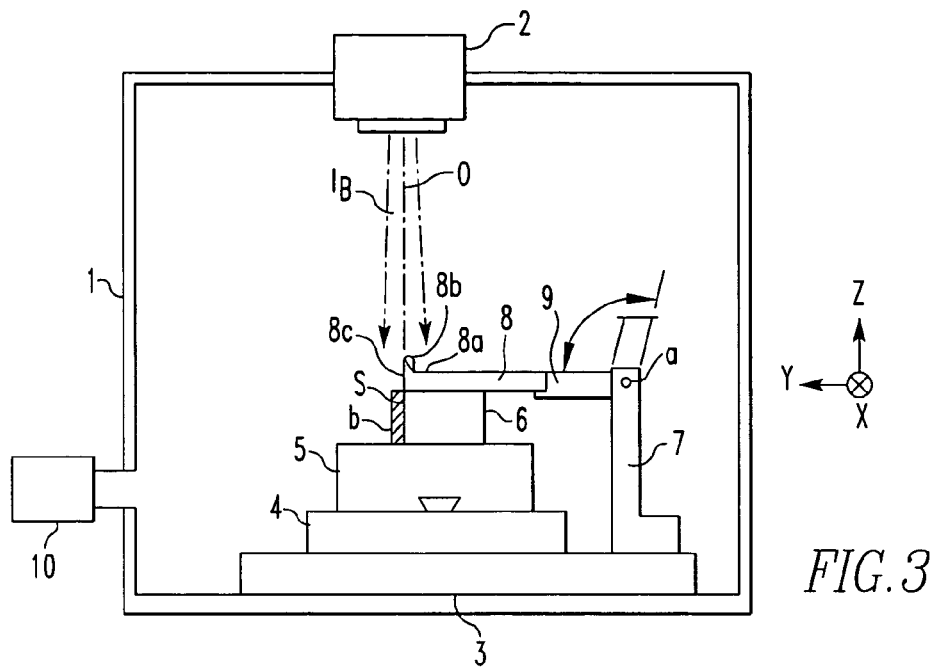
FIG. 3 is a schematic cross section of a sample preparation apparatus utilizing ion milling and built in accordance with the present invention.

FIG. 3 shows a sample preparation apparatus utilizing ion milling and built in accordance with the present invention. The apparatus has a vacuum chamber 1. An ion gun 2 is mounted on the top of the vacuum chamber 1. A gas ion gun is used as the ion gun 2. For example, the gas ion gun ionizes Ar gas by electric discharge and releases Ar ions.

The apparatus further includes a sample stage 3 on which an XY drive mechanism 4 capable of moving in the X- and Y-directions is disposed. A sample holder 5, which holds a sample 6, is set on the XY drive mechanism 4.

Referring still to FIG. 3, a mask drive mechanism 7 is disposed on the sample stage 3 and can move in the Y-direction. A mask-holding portion 9 holding a mask 8 made of a shielding material is mounted to the mask drive mechanism 7 so as to be tiltable about an axis a parallel to the X-axis. In the state shown in FIG. 3, the mask-holding portion 9 has been tilted toward the sample 6. The mask 8 is placed over the sample 6 and in intimate contact with it. A pumping system 10 evacuates the inside of the vacuum chamber 1.

Figure 4A:
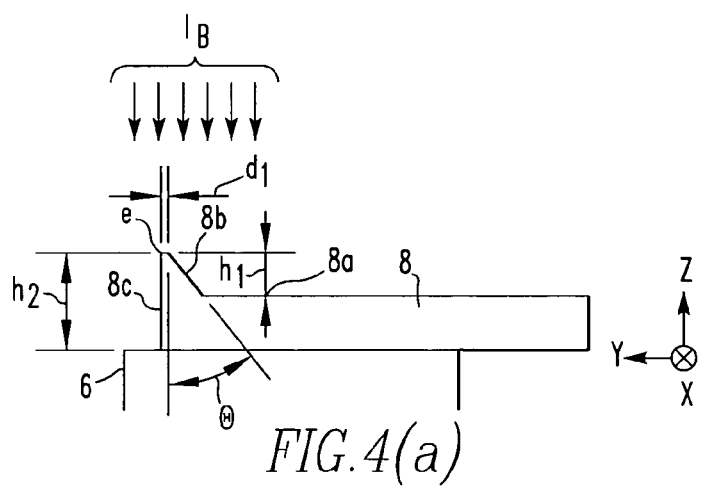
FIGS. 4(a) and 4(b) depict the mask shown in FIG. 3.
Figure 4B:
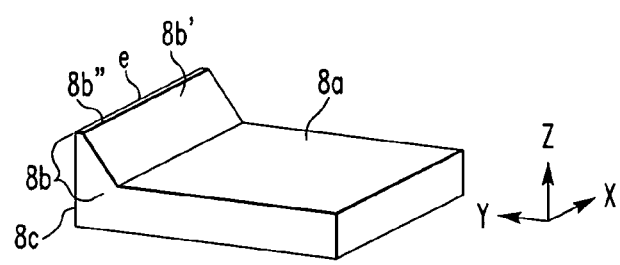

FIGS. 4(a) and 4(b) illustrate the mask 8 placed on the sample 6 shown in FIG. 3. FIG. 4(a) is a view as taken from a side (-X-direction) of the mask 8, and FIG. 4(b) is a perspective view of the mask 8.

Referring still to FIGS. 4(a) and 4(b), a surface 8a of the mask 8 is irradiated with the ion beam $I_B$ from the ion gun 2 and has an edge portion 8b that is thicker than the other portions. The thickness of the edge portion 8b increases with approaching its one edge e.

The edge portion 8b has a tilted surface 8b' parallel to the X-axis. The angle θ made between the tilted surface 8b' and the Z-axis is about 30 degrees. The thickness $h_1$ of the portion forming the tilted surface 8b' is about 0.5 mm. The top surface 8b" of the edge portion 8b is parallel to the XY-plane. The lateral width (length taken in the Y-direction) $d_1$ of the top surface 8b" is about 50 μm. The mask 8 is so machined that when it is brought into intimate contact with the sample surface, the side surface 8c of the mask 8 forms a plane that is substantially perpendicular to the sample surface. The thickness $h_2$ of the side surface 8c of the mask 8 is about 1.5 mm, which is greater than the thickness $h_2-h_1$ (=1 mm) of the flat portion.

The mask 8 can be fabricated, for example, by machining a magnetic material, such as Super Inver (Co—Ni alloy), into a shape as shown in FIGS. 4(*a*) and 4(*b*), and then firmly fixing an amorphous metal on the surface by nickel-phosphorus electroless plating (more than 10% phosphorus). The Super Inver is used for the following reasons. It has a quite small coefficient of thermal expansion. If the temperature rises due to ion beam irradiation, the resulting thermal deformation is small. The position of the edge varies little. Furthermore, it is easy to plate the material with a nickel-phosphorus alloy. The amorphous metal is used because during etching, the etching does not progress in a certain direction but progresses uniformly. The mask 8 can also be fabricated by machining a single-crystal material, such as sapphire, into a shape as shown in FIGS. 4(*a*) and 4(*b*). Thus, the structure of the sample preparation apparatus of FIG. 3 and the shape of the mask 8 for use in the preparation apparatus of FIG. 3 have been described in connection with FIGS. 4(*a*) and 4(*b*).

The sample 6 is machined by the ion beam with the sample preparation apparatus shown in FIG. 3 in the manner described below. In FIG. 3, the sample has a portion b to be etched to obtain a desired cross section S, the portion b being indicated by hatching. The mask and ion beam have been aligned relative to each other such that the side surface 8*c* of the mask 8 lies on the center axis O of the ion beam $I_B$.

First, the inside of the vacuum chamber 1 is pumped down to a given degree of vacuum by the pumping system 10. Then, the ion beam $I_B$ is emitted from the ion gun 2 and hits both the sample 6 and mask 8. The portion of the beam $I_B$ not shielded by the mask 8 etches the surface of the sample 6. That is, the processed portion b of the sample 6 is etched by the beam $I_B$ hitting the sample 6 with the boundary defined by the edge e of the mask 8.

Figure 5A:
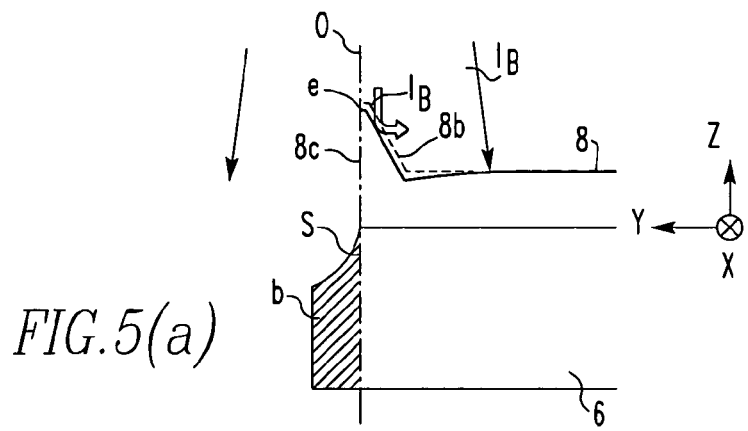
FIGS. 5(a)-5(c) illustrate a process in which a sample is etched by the apparatus shown in FIG. 3.
Figure 5B:
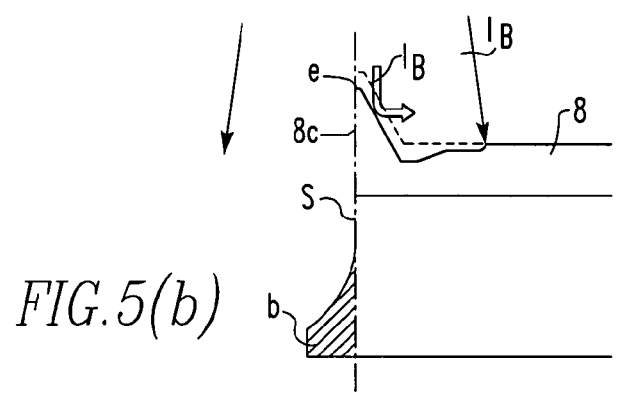
Figure 5C:
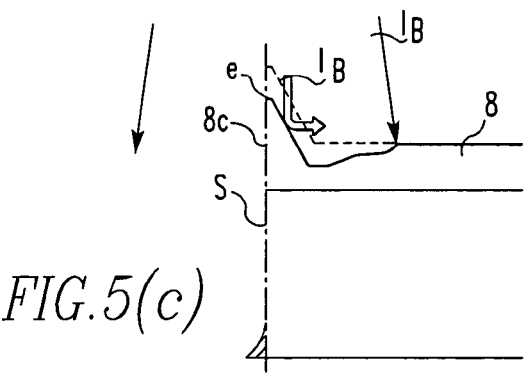

FIGS. 5(*a*) to 5(*c*) illustrate the process in which the processed portion b of the sample 6 is etched. The initial phase of the etching is shown in of FIG. 5(*a*). During this initial phase, the processed portion b of the sample 6 is etched from its one corner.

The portion of the mask irradiated with the ion beam $I_B$ is etched together with the sample. The edge portion 8*b* is tilted such that the thickness decreases with going away from the edge e and so ions hitting the top portion of the edge portion are reflected mainly away from the edge. As shown in FIG. 2(*d*) illustrating the ion path, it is less likely that the side surface of the mask is mainly etched. The original shape of the mask assumed prior to the irradiation of the ion beam is indicated by the broken line. As shown in FIG. 5(*a*), the edge portion 8*b* of the mask 8 irradiated with the beam $I_B$ is etched while the original shape is substantially maintained.

FIG. 5(*b*) shows a state occurring after a lapse of certain time since the state shown at in FIG. 5(*a*). In the state shown in FIG. 5(*b*), the edge portion 8*b* of the mask 8 has been etched further compared with the state shown in FIG. 5(*a*). However, the edge portion 8*b* of the mask 8 has been etched while the original shape assumed prior to the ion beam irradiation (indicated by the broken line) is substantially maintained. In particular, the thickness $h_2$ of the side surface 8*c* of the mask 8 has been reduced slightly by the ion etching. However, the side surface 8*c* of the mask 8 remains on the center axis O of the beam $I_B$. As a result, as shown in FIG. 5(*b*), the sample 6 is etched such that the desired cross section S appears.

Finally, the sample 6 and mask 8 are etched as shown in FIG. 5(*c*). As shown in FIG. 5(*c*), the edge portion 8*b* of the mask 8 has been etched while the original shape prior to the ion beam irradiation is substantially maintained. The side surface 8*c* of the mask 8 remains on the center axis O of the beam $I_B$. In consequence, a sample having the desired cross section S is prepared. The cross section S of the sample will be observed later with a scanning electron microscope or other instrument. The method of processing the sample 6 by the ion beam with the sample preparation apparatus of FIG. 3 has been described so far. Since the preparation apparatus of FIG. 3 uses the inventive mask shown in FIGS. 4(*a*) and 4(*b*), a sample having the desired cross section as described above and adapted for observation with an electron microscope can be prepared.

Figure 6A:
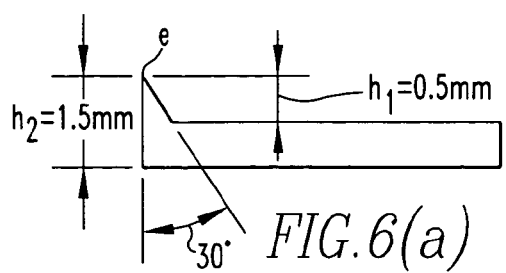
FIGS. 6(a) and 6(b) show a mask according to the present invention.
Figure 6B:
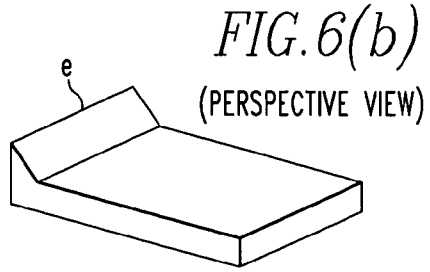

While one embodiment of the present invention has been described so far, the invention is not limited thereto. For example, the mask shown in FIG. 4(*b*) has the top surface 8*b*". As shown in FIGS. 6(*a*) and 6(*b*), a mask 8 having a sharp edge e not having the top surface 8*b*" may also be used. This mask shown in FIGS. 6(*a*) and 6(*b*) is similar to the mask shown in FIGS. 4(*a*) and 4(*b*) in other respects.

Our experiment has revealed that where the mask shown in FIGS. 6(*a*) and 6(*b*) is irradiated with the ion beam, the edge portion of the mask is etched as shown in FIGS. 7(*a*)-7(*e*), while the side surface of the mask is etched gradually. This experiment has shown that provision of the top surface 8*b*" on the mask as shown in FIGS. 4(*a*) and 4(*b*) is advantageous. Furthermore, the experiment has shown that the unirradiated side surface of the mask of FIGS. 6(*a*) and 6(*b*) is etched fully as shown in FIGS. 7(*a*)-7(*e*) but in a time longer than the time taken to fully etch the prior art mask shown in FIGS. 2(*a*)-2(*c*) by an amount corresponding to the increase in the thickness of the mask edge portion.

It is also to be understood that the present invention embraces a mask having an edge portion of a shape as shown in FIGS. 8(*a*) and 8(*b*). The edge portion of the mask shown in FIG. 8(*b*) has a rectangular cross section d. In contrast, in the embodiment described above, the cross-sectional shape is triangular.

It may be conceivable to make the thickness of the whole mask greater than conventional to achieve the object of the present invention. If such a mask is fabricated, the cost will be increased greatly. Accordingly, in the mask according to the present invention, only the edge portion is thickened.

Furthermore, the sample preparation apparatus according to the present invention may be used for preparation of samples observed with a transmission electron microscope, electron probe microanalyzer, Auger microprobe, or other similar instrument.

Having thus described our invention with the detail and particularity required by the Patent Laws, what is desired protected by Letters Patent is set forth in the following claims.

The invention claimed is:

1. A specimen preparation apparatus for ion milling away an edge of the specimen with an ion beam, comprising:
   a support for holding the specimen;
   an ion gun for directing the ion beam at the specimen held by the support;
   a mask for being placed in contact with a surface of the specimen, wherein the mask is a flat plate that covers the specimen except the edge thereof;
   means for placing the mask in contact with the surface of the specimen between the ion gun and the support so that the ion beam irradiates only the edge of the specimen and the edge of the mask; and
   the edge of said mask interrupting said beam determining a boundary between irradiated and unirradiated portions of the specimen, the edge of said mask being thicker than other portions of the mask and defining a plane intersecting the specimen surface, such that the edge of the mask irradiated with the ion beam is etched together with the specimen.

2. The specimen preparation apparatus for ion milling away an edge of the specimen with an ion beam according to claim 1, wherein an edge portion of the mask is tilted such that its thickness increases with approaching the edge of the mask.

3. The specimen preparation apparatus for ion milling away an edge of the specimen with an ion beam according to claim 1, wherein said edge of the mask has a flat side surface substantially perpendicular to the surface of the specimen.

* * * * *